(12) United States Patent
Jones et al.

(10) Patent No.: US 11,821,303 B2
(45) Date of Patent: Nov. 21, 2023

(54) ONE WAY TELEMETRY FOR COMMUNICATION OF DOWNHOLE DATA TO THE SURFACE USING NUCLEIC ACID

(71) Applicant: Halliburton Energy Services, Inc., Houston, TX (US)

(72) Inventors: Christopher Michael Jones, Katy, TX (US); Etienne Marcel Samson, Cypress, TX (US); Bin Dai, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 463 days.

(21) Appl. No.: 17/285,666

(22) PCT Filed: Nov. 19, 2018

(86) PCT No.: PCT/US2018/061813
§ 371 (c)(1),
(2) Date: Apr. 15, 2021

(87) PCT Pub. No.: WO2020/106270
PCT Pub. Date: May 28, 2020

(65) Prior Publication Data
US 2021/0355819 A1  Nov. 18, 2021

(51) Int. Cl.
*E21B 47/12* (2012.01)
*B01L 3/00* (2006.01)
*C12Q 1/6869* (2018.01)

(52) U.S. Cl.
CPC ........ *E21B 47/12* (2013.01); *B01L 3/502761* (2013.01); *C12Q 1/6869* (2013.01);
(Continued)

(58) Field of Classification Search
None
See application file for complete search history.

(56) References Cited

U.S. PATENT DOCUMENTS 9,322,056 B2   4/2016  McCann et al.
9,946,986 B1   4/2018  Saleri et al.
(Continued)

FOREIGN PATENT DOCUMENTS

WO   2016/004401 A1   1/2016

OTHER PUBLICATIONS

International Search Report and Written Opinion issued in related PCT Application No. PCT/US2018/061813 dated Aug. 19, 2019, 13 pages.
(Continued)

*Primary Examiner* — Carlos Garcia
(74) *Attorney, Agent, or Firm* — Conley Rose, P.C.; Rodney B. Carroll

(57) ABSTRACT

Encoding downhole data in nucleic acid molecules provides increased speed accuracy in the communication of downhole data to the surface. Nucleic acid molecules can be coded with downhole data using a telemetry module that comprises a microfluidic system to perform an encoding process that encodes carrier nucleic acid molecules with substitute sequences or segments at specific locations that comprise retrieved or acquired downhole data. The encoded carrier nucleic acid molecules are injected into a downhole fluid that is circulated to the surface. Once the encoded carrier nucleic acid molecules reach the surface, the information can be decoded and analyzed. Each carrier nucleic acid molecule may be preconfigured with a header. The header may comprise information that allows N for ease in coding and recombining downhole data.

20 Claims, 8 Drawing Sheets

(52) U.S. Cl.
CPC .............. *B01L 2200/0652* (2013.01); *B01L 2300/0816* (2013.01)

(56) References Cited

U.S. PATENT DOCUMENTS

2016/0215579 A1    7/2016  Van der Ende
2016/0371434 A1*  12/2016  Strauss ............ G01N 35/00871

OTHER PUBLICATIONS

De Silva, Pavani Yashodha, and Gamage Upeksha Ganegoda. "New trends of digital data storage in DNA." BioMed research international 2016 (2016).
Duncombe, Todd A., Augusto M. Tentori, and Amy E. Herr. "Microfluidics: reframing biological enquiry." Nature Reviews Molecular Cell Biology 16.9 (2015): 554-567.
Stovicek, Vratislav, Irina Borodina, and Jochen Forster. "CRISPR-Cas system enables fast and simple genome editing of industrial *Saccharomyces cerevisiae* strains." Metabolic Engineering Communications 2 (2015): 13-22.
Shibata, Mikihiro, et al. "Real-space and real-time dynamics of CRISPR-Cas9 visualized by high-speed atomic force microscopy." Nature communications 8.1 (2017): 1-9.
Karni, Moshe, et al. "Thermal degradation of DNA." DNA and Cell biology 32.6 (2013): 298-301.
"Subsurface DNA diagnostics aid well spacing decisions in the Permian", summary of article from World Oil, Mar. 22, 2018 found at http://www.worldoil.com/magazine/2018/March-2018/features/subsurface-dna-diagnostics-aid-well-spacing-decisions-in-the-permian, 2 pages.

* cited by examiner

ONE WAY TELEMETRY FOR COMMUNICATION OF DOWNHOLE DATA TO THE SURFACE USING NUCLEIC ACID

CROSS-REFERENCE TO RELATED APPLICATION

The present application is a U.S. National Stage Application of International Application No. PCT/US2018/061813 filed Nov. 19, 2018, which is incorporated herein by reference in its entirety for all purposes.

FIELD OF THE DISCLOSURE

The present disclosure generally relates to communication of downhole data to the surface and more particularly to one-way telemetry for communication of downhole data of a drilling system to the surface using nucleic acid, for example, deoxyribonucleic acid, ribonucleic acid, any other self-replicating molecules, or any combination thereof.

BACKGROUND

To recover downhole materials such as hydrocarbons from geological formations it is common to drill a well from the surface into the formation. The well is drilled into the ground and directed to the targeted geological location from a drilling rig at the surface. Typically, the drilling rig rotates a drillstring so as to rotate a bottom hole assembly (BHA) that includes a drill bit connected to the lower end of the drillstring. During drilling, a drilling fluid, commonly referred to as drilling mud, is pumped and circulated down the interior of the drillpipe, through the BHA and the drill bit, and back to the surface in the annulus.

During drilling, various downhole measurements may be obtained, and such is commonly referred to as logging while drilling (LWD). These measurements or data are typically communicated to the surface using mud telemetry. Mud telemetry is fairly slow and not conducive to the communicative of large amounts of data. Additionally, the pressure pulses used in mud telemetry disperse over the mud column and do not stay coherent enough to send data at a high rate. As the amount of the data that can be sent to the surface is restricted by the rate of transmission, large amounts of data may be stored locally in memory on the downhole tool. The data may not be accessible until the downhole tool is retrieved. Retrieving a downhole tool may take time and may be expensive. Further, the data retrieved from the downhole tool is not real time data. Thus, a system is needed to provide transmission of large amounts of downhole data to the surface accurately and in real time or close to real time without requiring retrieval of the downhole tool.

BRIEF DESCRIPTION OF THE DRAWINGS

For a detailed description of the embodiments of the invention, reference will now be made to the accompanying drawings in which.

DETAILED DESCRIPTION

Figure 1:
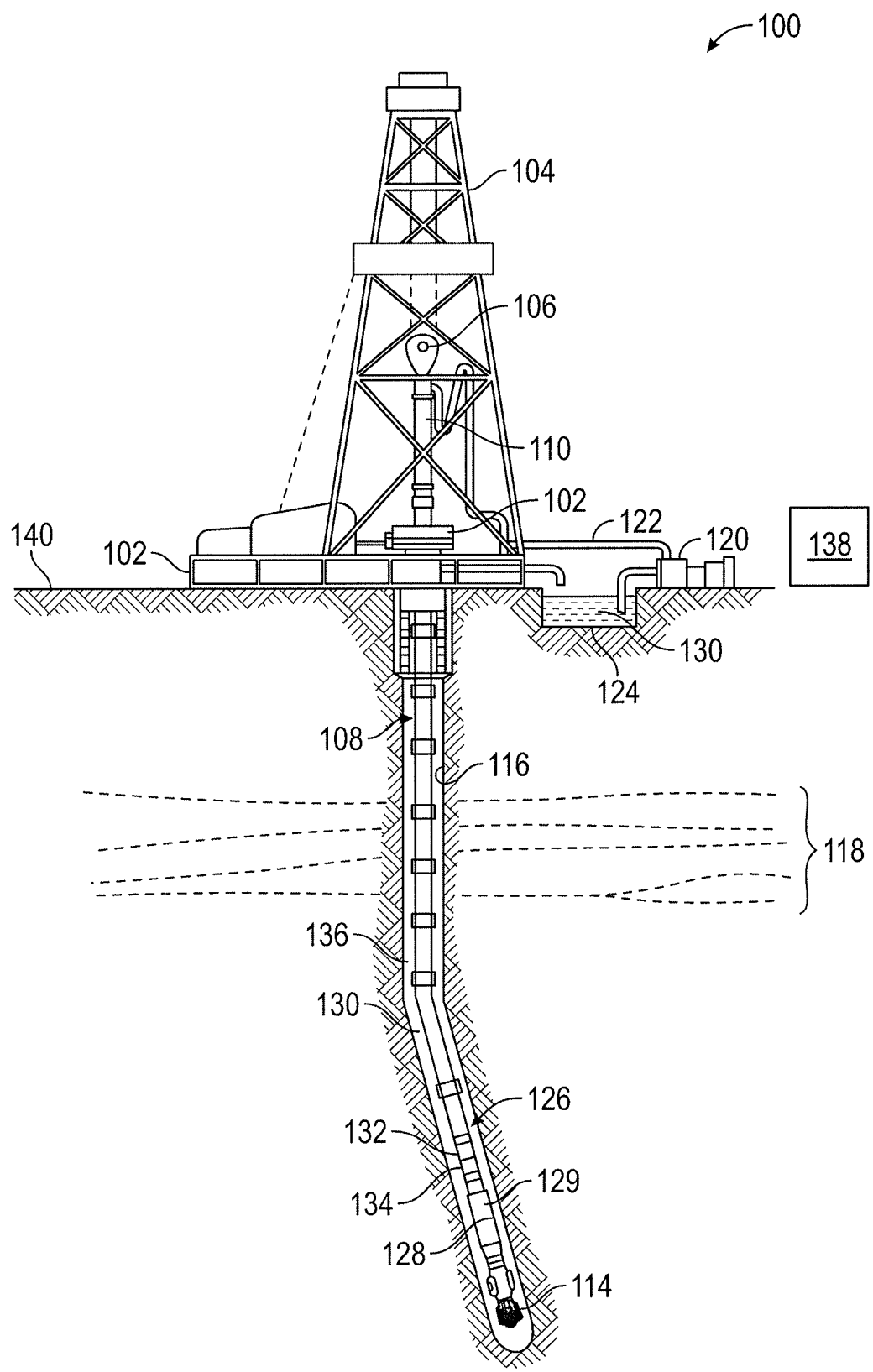
FIG. 1 depicts a schematic view of a drilling system, according to one or more aspects of the present disclosure.

Telemetry rates for transmitting information or data from a downhole drilling tool to a surface receiver are generally slow, unreliable, expensive or any combination thereof. Typically, the transmission of downhole data utilizes mud telemetry such as mud pulse methods or mud siren methods, short hop electromagnetic methods, or wired pipe. Methods of permanent emplacement telemetry include wired completions, fiber optics or tracers. Wired completions and tracers provide an advantage over mud telemetry in that these methods have increased speed and bandwidth of communication. However, wired completions and tracers also require that the well is initially outfitted with such capability where the installation cost may be expensive. A retrofit may be available for tracer methods but generally tracers only provide information as to the state of a system such as water influx. That is, tracers provide only a binary state.

The present invention relates generally to one-way telemetry for increased speed and bandwidth of the communication of downhole data to the surface using deoxyribonucleic acid (DNA), ribonucleic acid (RNA), any other self-replicating molecule or any combination thereof (referred to herein for simplicity as "nucleic acids"). In one or more embodiments, the nucleic acids may comprise DNA, RNA or both where any combination thereof is referred to herein as a nucleic acid. According to one or more aspects of the present inventions, a nucleic acid segment or section of a nucleic acid strand is used as a method of information telemetry or communication in which data or information is coded to the nucleic acid segment or section downhole and released or injected into the natural flow of fluids pumped downhole and recovered at the surface, for example, drilling mud. A nucleic acid segment or section has the potential to code very large quantities of information and nucleic acid can survive harsh downhole environmental conditionals such as high temperatures and a chemical environment. For example, thermophiles can survive and multiply above 110 degrees Celsius with degradation occurring above 190 degrees Celsius and full degradation occurring at 210 degrees Celsius within thirty minutes. The nucleic acid segment or section may be pre-coded with a header that comprises header information including date-time sequences, position sequence and downhole tool sequences or any combination thereof. Amplification of nucleic acid by polymerase chain reaction (PCR) methods is inherently sensitive to infinitesimally small quantities of nucleic acid segments or sections. Therefore, recovery of only a small quantity of nucleic acid segments or sections is required to self-replicate the nucleic acid segments or sections and decode the downhole information contained in the one or more nucleic acid segments or sections. Although PCR is the present state of the art for replication of biological self-replicating molecules outside a biological system, the present disclosure contemplates any other one or more self-replication methods suitable for use with the claimed invention.

Coding downhole information or data in nucleic acid segments or sections provides an improved communication of downhole data or information to the surface. The coded nucleic acid segments or sections of nucleic acid strands not only withstand downhole conditions but also provide for the communication of large amounts of downhole information or data in real time or near real time. In addition, current drilling systems may be efficiently and inexpensively retrofitted to include encoding of nucleic acid strands. Further, nucleic acid strands provide an inexpensive alternative to traditional communication methods.

In one or more aspects of the present disclosure, a well site operation may utilize an information handling system to control one or more operations including, but not limited to, retrieval of information or data from nucleic acid strands communicated via fluid circulated downhole. For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components. The information handling system may also include one or more interface units capable of transmitting one or more signals to a controller, actuator, or like device.

For the purposes of this disclosure, computer-readable media may include any instrumentality or aggregation of instrumentalities that may retain data and/or instructions for a period of time. Computer-readable media may include, for example, without limitation, storage media such as a sequential access storage device (for example, a tape drive), direct access storage device (for example, a hard disk drive or floppy disk drive), compact disk (CD), CD read-only memory (ROM) or CD-ROM, DVD, RAM, ROM, electrically erasable programmable read-only memory (EEPROM), and/or flash memory, biological memory, molecular or deoxyribonucleic acid (DNA) memory as well as communications media such wires, optical fibers, microwaves, radio waves, and other electromagnetic and/or optical carriers and/or any combination of the foregoing.

Illustrative embodiments of the present disclosure are described in detail herein. In the interest of clarity, not all features of an actual implementation may be described in this specification. It will of course be appreciated that in the development of any such actual embodiment, numerous implementation-specific decisions must be made to achieve the specific implementation goals, which will vary from one implementation to another. Moreover, it will be appreciated that such a development effort might be complex and time-consuming but would nevertheless be a routine undertaking for those of ordinary skill in the art having the benefit of the present disclosure.

Turning now to the figures, FIG. 1 depicts a schematic view of a drilling operation utilizing a drilling system 100, according to one or more aspects of the present invention. In one or more embodiments, the drilling system 100 may be a directional drilling system. While the drilling system 100 of the present disclosure illustrates a land-based drilling system, the present disclosure contemplates any drilling system, such as an offshore or subsea well or a on shore or land well. Further, it will be understood that the present disclosure is not limited to only drilling a hydrocarbon, such as natural gas or oil, well. The present disclosure also encompasses wellbores in general, for example, for water. Further, the present disclosure may be used for the exploration and formation of geothermal wellbores intended to provide a source of heat energy instead of hydrocarbons. While FIG. 1 is discussed herein as an illustrative embodiment, the present disclosure contemplates any system or environment where fluid is flowed from downhole to a surface. For example, one or more embodiments may be directed to hydraulic stimulation flow back, coiled tubing treatment flow back, permanent placement sensor communication or any combination thereof.

FIG. 1 shows a tool string 126 disposed in a borehole or well bore 116. In one or more embodiments, the tool string 126 includes a downhole tool 128. Downhole tool 128 may comprise a bottom hole assembly (BHA) or be part of a BHA. A drilling platform 102 supports a derrick 104 having a traveling block 106 for raising and lowering a drill string 108. A kelly 110 supports the drill string 108 as the drill string 108 is lowered through a rotary table 112. In one or more embodiments, a topdrive is used to rotate the drill string 108 in place of the kelly 110 and the rotary table 112. A drill bit 114 is positioned at the downhole end of the tool string 126, and, in one or more embodiments, may be driven by a downhole motor 129 positioned on the tool string 126, by rotation of the entire drill string 108 from the surface or both. As the drill bit 114 rotates, the drill bit 114 creates the borehole 116 that passes through various formations 118. A pump 120 circulates fluid 130 through a feed pipe 122, for example, drilling fluid (such as mud), water, any other fluid or combination thereof and downhole through the interior of drill string 108, through orifices in drill bit 114, back to the surface via the annulus 136 around drill string 108, and into a retention pit 124. The fluid 130 transports cuttings from the borehole 116 into the pit 124 and aids in maintaining the integrity of the borehole 116. The fluid 130 may also drive the downhole motor 129.

The tool string 126, the downhole tool 128, or both may include one or more logging while drilling (LWD) or measurement-while-drilling (MWD) tools 132 that collect one or more measurements or information relating to any one or more of various downhole conditions, borehole and formation properties as well as the position of the drill bit 114 and various other drilling conditions as the bit 114 extends the borehole 108 through the formations 118. The LWD/MWD tool 132 may include a device for measuring formation resistivity, a gamma ray device for measuring formation gamma ray intensity, devices for measuring the inclination and azimuth of the tool string 126, pressure sensors for measuring fluid pressure, temperature sensors for measuring borehole temperature, or any other downhole tool or combination thereof.

The tool string 126 may also include a telemetry system 134. Telemetry system 134 may comprise a nucleic acid encoding or substitution system for a nucleic acid encoding technology as discussed with respect to FIGS. 2-8. In one or more embodiments, the nucleic acid encoding system, for example nucleic acid encoding system 260 of FIG. 2, may comprise a clustered regularly interspaced short palindromic repeats (CRISPR)-associated protein-9 nuclease (Cas9) (hereinafter, CRISPR/Cas9) substitution method or technology as illustrated in FIG. 8, or any other substitution method or technology. The telemetry system 134 receives data provided by the various sensors of the tool string 126 (for example, sensors of the LWD/MWD tool 132), and transmits the data to a surface control unit 138 by encoding the data as one or more nucleic acid segments or sections into a standard nucleic acid chain and dispersing the substituted or coded carrier nucleic acid segments or sections of a nucleic acid strand in the fluid 130 for communication to the surface 140 according to one or more aspects of the present disclosure. Data may also be provided by the surface control unit 138, received by the telemetry system 134, and transmitted to the tools (for example, LWD/MWD tool 132, downhole tool 128, or any other tool) of the tool string 126. In one or more embodiments, the surface control unit 138 may communicate directly with the LWD/MWD tool 132, the downhole tool 128 or both. The surface control unit 138 may be an information handling system, for example, an information handling system 700 of FIG. 7, stationed at the well site, a portable electronic device, a remote computer, or distributed between multiple locations and devices. The surface control unit 138 may also be a control unit that controls functions of equipment of the tool string 126.

The downhole tool 128 may be configured to change the direction of the tool string 126, the drill bit 114 or both, such as based on information communicated to the surface 140 via one or more of the nucleic acid segments or sections dispersed in the fluid 130 by the telemetry system 134. In one or more embodiments, the downhole tool 128 is coupled to the drill bit 114 and drives rotation of the drill bit 114. In one or more embodiments, the downhole tool 128 rotates in tandem with the drill bit 114. In one or more embodiments, the downhole tool 128 is a point-the-bit system or a push-the-bit system.

Figure 2:
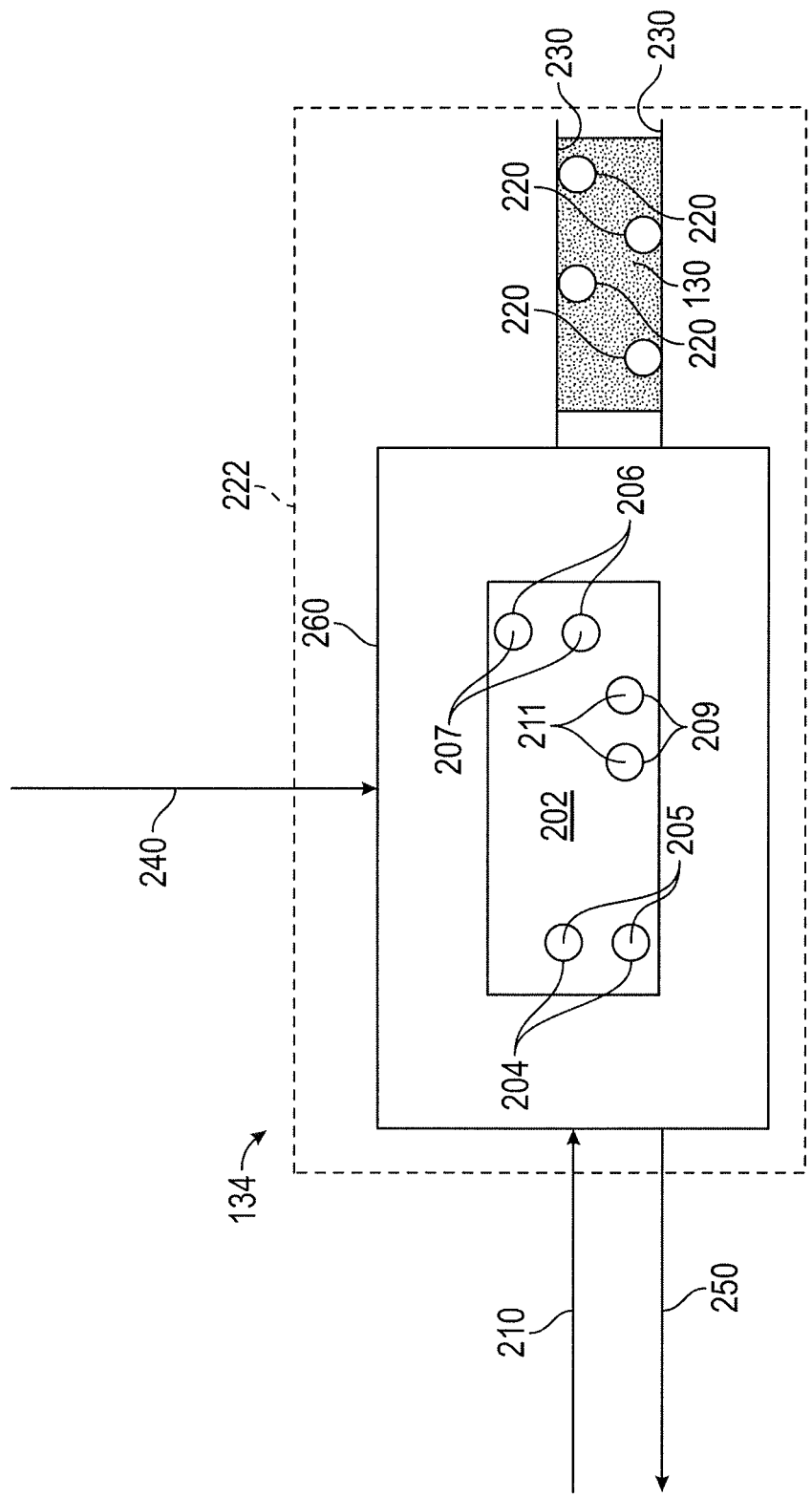
FIG. 2 depicts a block diagram of a telemetry system, according to one or more aspects of the present disclosure.

FIG. 2 depicts a block diagram of a telemetry system 134, according to one or more embodiments of the present disclosure. The telemetry system 134 may comprise one or more input data lines 210, one or more output data lines 250, one or more output ports 230, one or more surface data lines 240 and a nucleic acid encoding system 260. The one or more input data lines 210 may receive downhole data or information from any one or more downhole tools or sensors and transmit the data or information to the nucleic acid encoding system 260. In one or more embodiments, the nucleic acid encoding system 260 may comprise an encoder 202, for example, microfluidic chip 510 of FIG. 5, coupled to a control system 222, for example, information handling system 700 of FIG. 7, or both. The encoder 202 may comprise a first repository 204 comprising one or more self-replicating molecule segments 205, for example, one or more nucleic acid segments or sections 205, a second repository 206 comprising one or more carrier nucleic acid strands 207, and a third repository 209 comprising one or more activation substances 211. The activation substances 211 may include any substance known in the art that promotes nucleic acid editing, nucleic acid self-replication or both. In one or more embodiments, the first repository 204, the second repository 206, and the third repository 209 may comprise any number of repositories. For example, in one embodiment, the activation substances that promote nucleic acid editing and the activation substances that promote nucleic acid self-replication may be divided into one or more repositories.

The control system 222 may direct or otherwise instruct the encoder 202 to select one or more nucleic acid segments 205 that represent the downhole data or information, mix with one or more carrier nucleic acid strands 207 and the one or more activation substances 211, and perform nucleic acid encoding, pursuant to a nucleic acid editing method or technology, for example, CRISPR/Cas9, in order to form one or more encoded carrier nucleic acid segments (not shown) of an encoded carrier nucleic acid strand 220. In one or more embodiments, the nucleic acid encoding system 260 may receive surface data or information from the surface via one or more surface data lines 240. Nucleic acid encoding system 260 may output data or information to one or more downhole tools via one or more output data lines 250. In one or more embodiments, the nucleic acid encoding system 260 may communicate or flow the one or more encoded carrier nucleic acid sections or segments (not shown) of one or more encoded carrier nucleic acid strands 220 to the surface 140 in a fluid 130 via one or more output ports 230.

Figure 3:
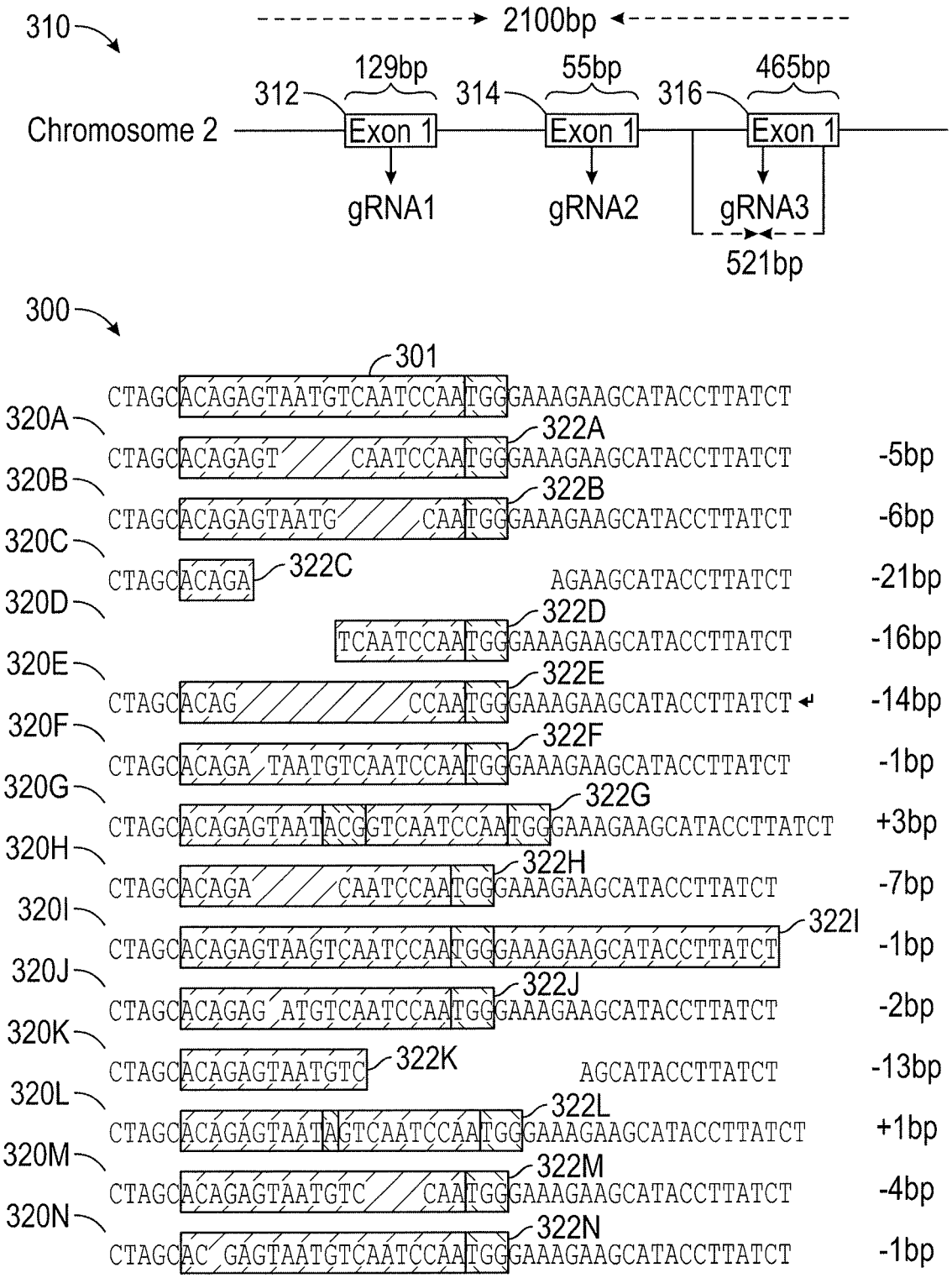
FIG. 3 depicts an example encoded DNA strand, according to one or more aspects of the present disclosure.

FIG. 3 depicts an example base carrier DNA strand 300, according to one or more aspects of the present disclosure. The base carrier strand is also shown as chromosome 2 310 having a length of 2100 base pairs (bp) with three locations 312, 314, and 316 primed for substitution of a DNA segment encoded with downhole information. The substitute portion 301 of the base carrier DNA strand 300 corresponds with one of the three locations 312, 314, and 316 primed for substitution. Each of the lines 320A-N illustrate an encoded carrier DNA strand that is configured to contain telemetry information, for example, data or information from one or more downhole tools or sensors. The encoded portions 322A-N in these encoded strands 320A-N represent DNA segments that have replaced one of the three locations 312, 314, or 316 that have been primed for substitution. These encoded portions 322A-N are encoded with downhole information. In some embodiments, the encoded portions 322A-N may vary in length depending on the type and volume of downhole information contained therein and need not be the same length as the substitute portion 301. For example, encoded portion 322A is 5 bp less than the substitute portion 301, resulting in an encoded carrier DNA strand that is 2095 bp. In some embodiments, more than one substitutions of DNA segments encoded with downhole information may be performed. For example, multiple substitutions have been performed in encoded DNA carrier strand 320G.

Figure 4:
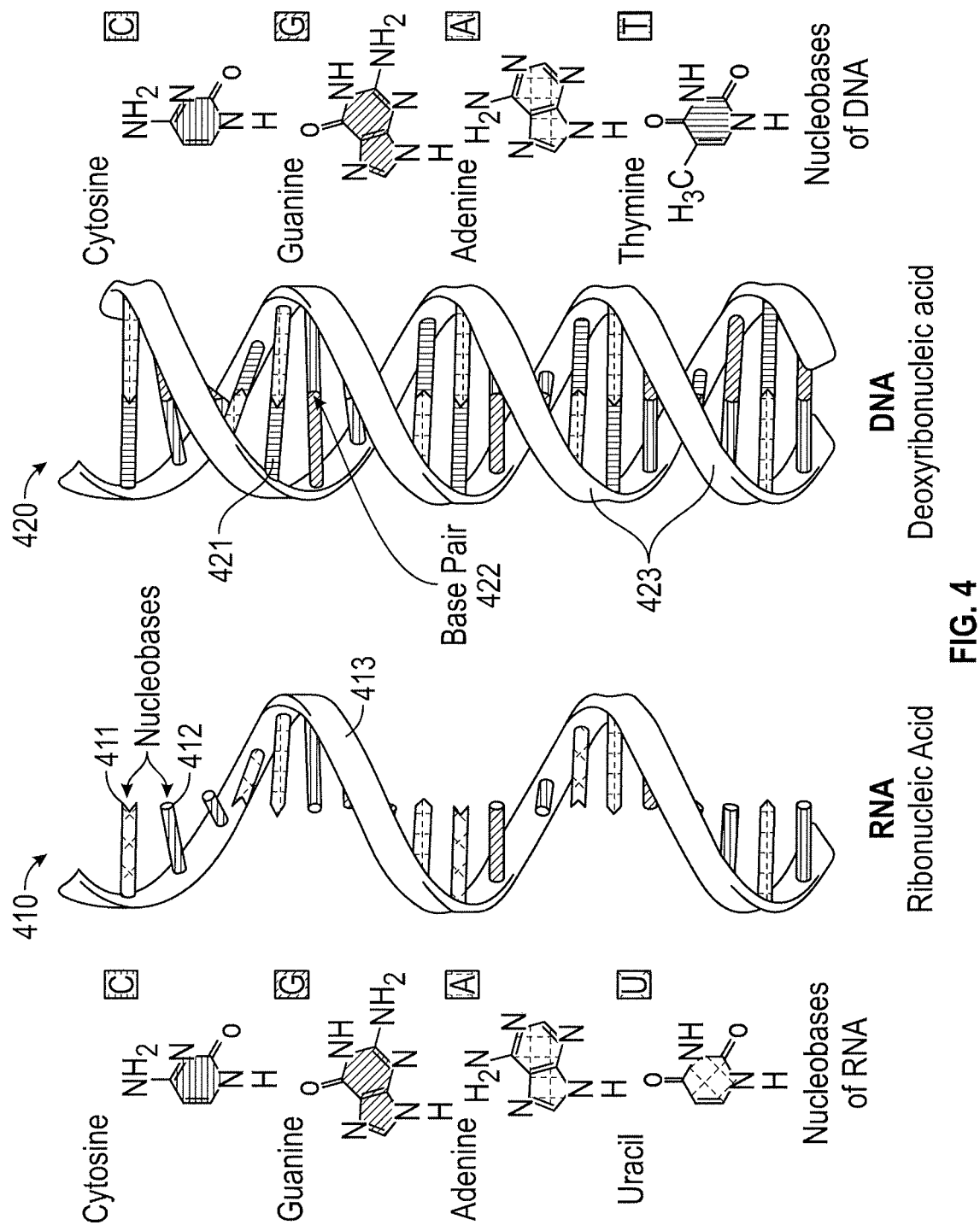
FIG. 4 depicts an example coded RNA strand, according to one or more aspects of the present disclosure.

FIG. 4 depicts an example portion of a RNA molecule 410 and DNA molecule 420, encoded with downhole information, according to one or more aspects of the present disclosure. RNA molecules 410 are formed by a series of nucleobases, for example, nucleobases 411 and 412, along a helix backbone 413 while DNA molecules 420 are formed by a series of paired nucleobases, or base pairs 421 and 422, along a double helix backbone 423. In some embodiments, any combination of nucleobases 411 and 412 or base pairs 421 and 422 may encode downhole information that may be decoded at the surface.

Figure 5:
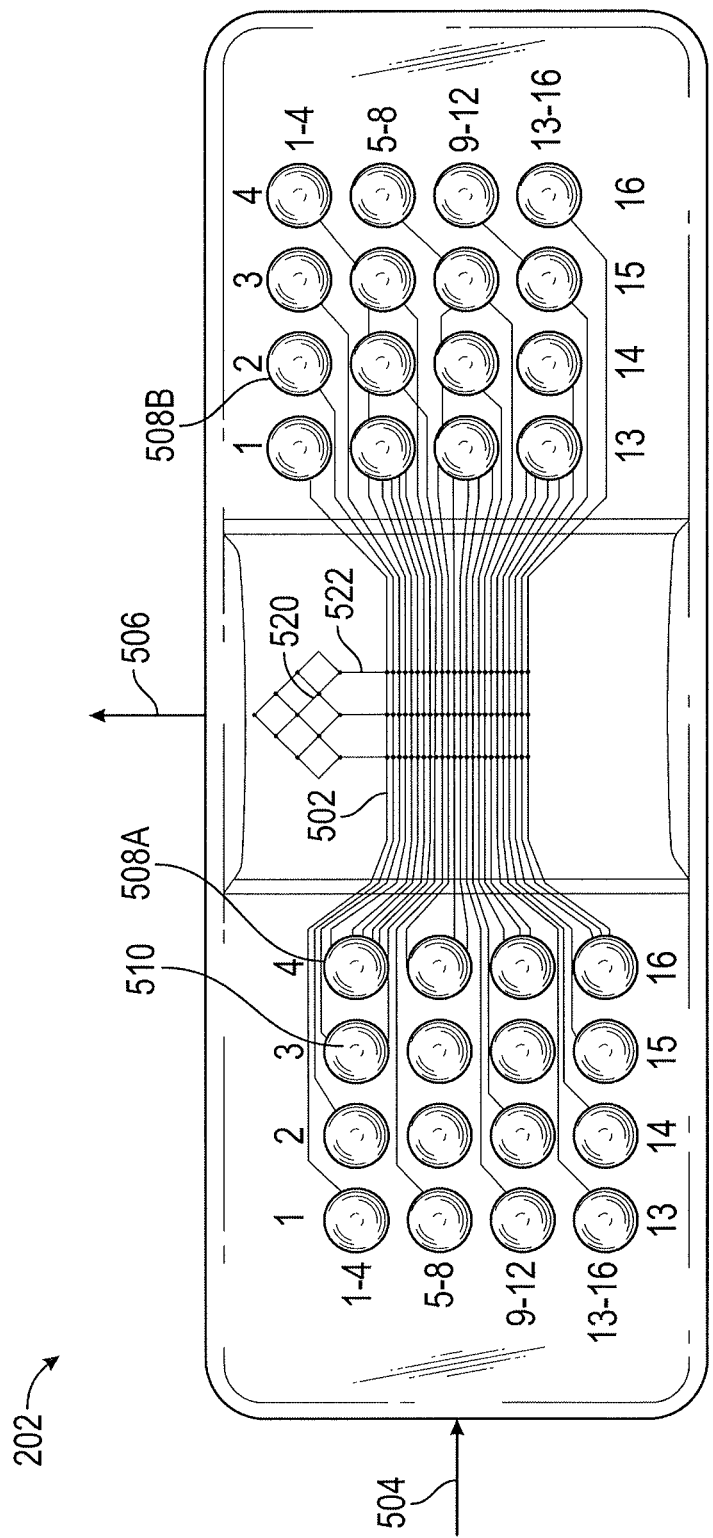
FIG. 5 depicts a microfluidic chip for encoding one or more nucleic acid segments or sections of a nucleic acid strand, according to one or more aspects of the present disclosure.

FIG. 5 depicts a microfluidic chip 202 for encoding one or more nucleic acid segments or sections of a nucleic acid strand, according to one or more aspects of the present disclosure. The microfluidic chip 202 of the illustrated embodiment comprises one or more micro-channels 502 coupled together. Microfluidic chip 202 comprises one or more inputs 504 and one or more outputs 506. In one or more embodiments, the one or more inputs 504 are coupled to one or more input lines 210 of FIG. 2 and the one or more outputs 506 are coupled to one or more output ports 230 of FIG. 2. The microfluidic chip 202 may comprise any number of repositories 508. Any one or more repositories 508 may comprise a fluid containing any number of substances 510. For example, the fluid 510 may comprise one or more nucleic acid segments or sections, one or more carrier nucleic acid strands, one or more activation substances, or one or more contrast agents such as, but not limited to, fluorescent markers, or ferrofluid markers. As shown in the illustrated embodiment, each repository 508 may be connected to a micro-channel 502 and each repository 508 may eject any substance contained therein into its associated micro-channel 502. The microfluidic chip 202 of FIG. 5 comprises a 16×16 microfluidic chip. However, the present disclosure contemplates any other dimensions for microfluidic chip 202. In one or more embodiments, the microfluidic chip 202 may comprise any number of repositories 508 and micro-channels 502.

The microfluidic chip 202 may also comprise one or more components necessary for performing the encoding of data or information in the one or more nucleic acid segments or sections 204. For example, the microfluidic chip 202 may comprise one or more components required to perform a substitution method, for example, CRISPR/Cas9 substitution including, but not limited to, one or more components required to open and/or close any one or more of the nucleic acid segments or sections 204, a temperature component, any other required component or any combination thereof. In one or more embodiments, the microfluidic chip 202 comprises a mixing component 520 for mixing one or more fluids 510 from the one or more repositories 508. As shown, the mixing component 520 may include channels 522 that intersect with the micro-channels 502. Each intersection of the channels 522 of the mixing component 520 with the micro-channels 502 may include valve control, a pump control, or both, for isolating or opening any one or more of the micro-channels 502 to the mixing component 520, and/or for diverting flow along any micro-channel 502 to the mixing component 520. As one of ordinary skill in the art may appreciate, the microfluidic chip 202 is representative of only one potential configuration that may achieve mixing of the substances 510 ejected from various repositories 508. Encoding may be performed alternatively on any type of micro-fluidic and/or lab-on-a-chip technology known in the art.

Figure 6:
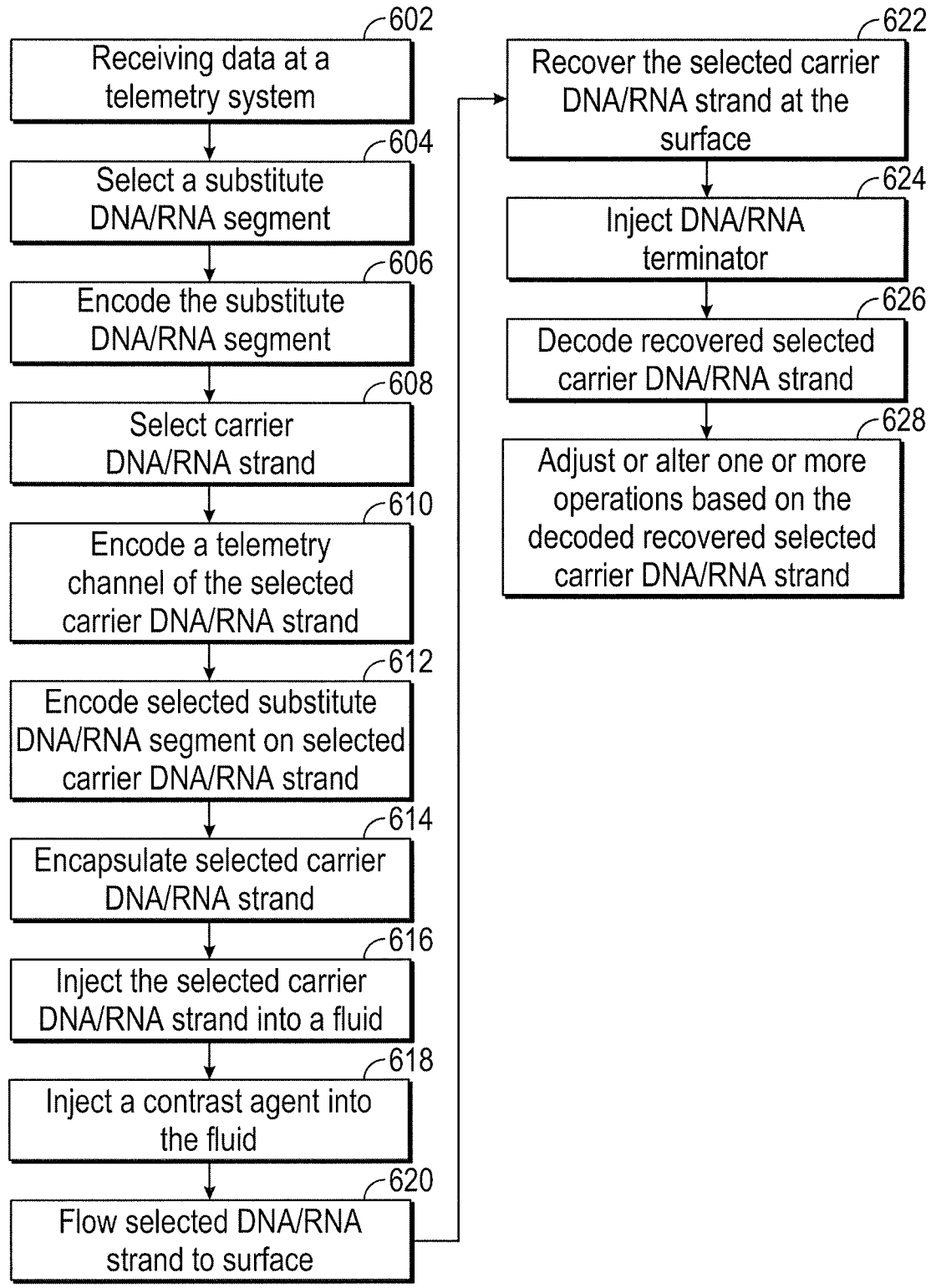
FIG. 6 depicts a flowchart of an example method for encoding a nucleic acid strand, according to one or more aspects of the present disclosure.

FIG. 6 depicts a flowchart of an example method for encoding a nucleic acid strand, according to one or more aspects of the present disclosure. Utilizing a nucleic acid encoding system including, but not limited to, a microfluidic system operated according to a substitution protocol, for example, CRISPR/Cas9 substitution protocol, one or more selected carrier nucleic acid sections or segments, for example, a selected carrier DNA/RNA section or segment, of a nucleic acid strand, for example, a DNA/RNA strand, may be substituted with a nucleic acid section or segment, for example, a substitute self-replicating DNA/RNA section or segment, encoding information acquired downhole via any one or more downhole tools, for example, downhole tool 128 of FIG. 1 to form one or more encoded carrier nucleic acid segments or sections, for example, an encoded carrier DNA/RNA segment or section, of one or more carrier nucleic acid strands, for example, a carrier DNA/RNA strand.

In one or more embodiments, data from one or more downhole tools is transmitted to a control system, for example, control system 260 of FIG. 2 of a telemetry system 134, of a microfluidic nucleic acid encoding technology for encoding downhole information. For example, at step 602, a control system 260 receives a set of instructions or commands such as to operate the nucleic acid encoding technology or method, for example to encode downhole information for communication to the surface. For example, the telemetry system 134 receives information or data from one or more downhole tools, downhole sensors, downhole devices, or any other downhole measurement system via one or more input lines 210 as illustrated in FIG. 2. At step 604, the control system 260 of telemetry system 134 acquires or selects one or more substitute nucleic acid sections or segments encoded with the downhole information according to a predetermined protocol, such as, from a first repository 508 of FIG. 5. For example, in a 128-bit system that has 128 nucleic acid substitute sequences, each segment or section may correspond to one bit out of the 128 bit system or a larger or smaller bit system that is convened may be used. A position or location within the nucleic acid strand that the nucleic acid segments are substituted to may be predetermined according to the predetermined protocol. At step 606, the received downhole information is encoded on one or more nucleic acid strand using a predetermined substitution method or technology. For example, the one or more nucleic acid sections or segments encoded with downhole information may be inserted using CRISPR/Cas9 protocol or any other substitution protocol.

In one or more embodiments, a step 606 may comprise selecting from a first repository 508 a carrier nucleic acid strand, selecting from a second repository 508 a nucleic acid segment or section and selecting an activation substance from third repository 508. A nucleic acid encoding method or technology mixes the carrier nucleic acid strand, the nucleic acid segment or section and the activation substance that promotes encoding. The nucleic acid segment is encoded with data or information that is to be communicated to the surface. In one or more embodiments, the nucleic acid segment or section may be fabricated downhole or may be predetermined before disposing the downhole tool within a wellbore. In one or more embodiments, the one or more activation substances may comprise one or more combinations of chemicals. In one or more embodiments, the activation substance comprises one or more chemicals in combination with a heat element.

The carrier nucleic acid strand and/or the nucleic acid segment or section may be precoded with a header. The header comprises header information associated with one or more parameters. For example, one or more parameters may comprise date, time, downhole location, tool type, downhole tool identifier (for example, a unique identifier may be associated with each downhole tool or group of downhole tools), one or more preconfigured status signals, or any combination thereof. The header also allows the information encoded on the carrier nucleic acid strand to be sorted, decrypted, or otherwise processed based, at least in part on the header. For example, in one or more embodiments, only information coded on selected carrier nucleic acid strands with a header that comprise a header indicative of information from a predetermined time period may be utilized for processing at the surface. Information associated with a header that meets a predetermined criteria, range or threshold may be used to alter or adjust one or more drilling operations (such as direction of the drill bit), fluid being pumped downhole, or any other parameter or operation. For example, the header may comprise time information. The time information may indicate a time period for the associated information coded on the carrier nucleic acid strands so that at the surface only the information within a time period of interest need be decoded. In this manner, the coded carrier nucleic acid strands that have accumulated at the surface may be selectively decoded based on the header information. A header allows for parallelization of a plurality of channels, for example, conveying information from more than one tool downhole and reconstruction of those channels once the carrier nucleic acid strand reaches the surfaces. In one or more embodiments, the header is pre-coded or preconfigured in the nucleic acid strand to save time in the encoding process. For example, the header may be pre-coded or preconfigured in the nucleic acid strands at the surface prior to disposing or positioning the downhole tool in the borehole or well bore. In one or more embodiments, the telemetry system 134 selects a carrier nucleic acid strand based, at least in part, on the corresponding or desired pre-coded or preconfigured header. In one or more embodiments, the telemetry system 134 codes on a carrier nucleic acid strand header information of a header in real time by substitution. In one or more embodiments, a header is not required, and the encoding method or technology inserts the nucleic acid section or segment to form the encoded carrier nucleic acid strand without any header.

In one or more embodiments, a substitution method or technology is implemented such that the selected self-replicating nucleic acid section or segment may be substituted or coded on the selected carrier nucleic acid strand at specific locations of the selected carrier nucleic acid strand. For example, the substitution process may require an encoder 202 of FIG. 2 to write retrieved or acquired data on a corresponding carrier nucleic acid strand. The selected carrier nucleic acid strand is opened, the required information or the nucleic acid section or segment is written to the specified carrier nucleic acid segment, the nucleic acid strand is closed, for example, according to a CRISPR/Cas9 protocol. In one or more embodiments, the substitution process is performed on a plurality of segments of the selected carrier nucleic acid strand at the same time or at substantially the same time such that multiple substitutions of nucleic acid segments or sections are performed on the selected carrier nucleic acid strand in the time required to perform a single substitution process. For example, coding or substitution may occur in parallel, encoding information from a plurality of data streams by utilizing unique header information. Performing a plurality of substitutions during a substitution process may increase bit rate.

In one or more embodiments, the encoding process may comprise encoding any one or more sections or segments of the carrier nucleic acid strand utilizing CRISPR or any other suitable technique or process. In one or more embodiments, a single nucleic acid section or segment or a plurality of nucleic acid sections or segments may be introduced into the selected carrier nucleic acid strand allowing a base significantly higher than binary, even hexadecimal. For example, 256-bit nucleic acid sections or segments may exist allowing eight bit strings to be coded with a single substitution thereby speeding the coding process by a factor of eight times over a binary code. Different carrier nucleic acid strands may have different substitution speeds or time required to encode a nucleic acid section or segment into a selected carrier nucleic acid strand.

In one or more embodiments, at step 614 carrier nucleic acid strands may be encapsulated to provide protection from the fluid and to ensure mitigation of dispersion. For example, the carrier nucleic acid sections or segments may be encapsulated in a contrast agent, a ferrofluidic fluid or capsule, a solid capsule, any other encapsulation capsule, fluid or agent, or any combination thereof. In one or more embodiments, the injection of the one or more encoded carrier nucleic acid strands may occur based on a predetermined condition. For example, a predetermined condition may comprise any one or more of a timed interval (for example, every thirty minutes), completion of a substitution, once a certain amount of data or information has been substituted, predetermined depth intervals, comparison of a downhole condition (for example, temperature) to a predetermined threshold, or at any other timing, or based on any other condition or criteria. The contrast agent may make recovery at the surface easier. For example, a fluorescent sensor may look for the fluorescent contrast agent at the surface and isolate the segments of fluid that have the contrast agent. Further, a magnet may be used to rapidly separate the carrier nucleic acid strands encapsulated in a ferromagnetic fluid. The encapsulation process may be completed by information handling system or other system, for example, the telemetry system 134, control system 260, or both.

After substituting one or more nucleic acid sections or segments into one or more corresponding carrier nucleic acid strands (and in one or more embodiments, encapsulating the carrier nucleic acid strands), at step 616 the corresponding one or more carrier nucleic acid strands are injected or otherwise introduced into a fluid, for example, fluid 130 of FIG. 1. In one or more embodiments, a combination of carrier nucleic acid strands may be injected into the fluid 130. In some embodiments, the combination of carrier nucleic acid strands may provide the complete communication. For example, each carrier nucleic acid strand may be considered like a page in a book with each substitution akin to writing letters on a page of the book and each strand representing a page of the book. The information in the header may be considered to correspond to a page number in the book or any other information about the book. In one or more embodiments, at step 618 a contrast agent may be injected into the fluid. The contrast agent may identify at the surface the nucleic acid rich portion of the fluid. For example, a contrast agent may comprise a fluorescent marker.

At step 620, the one or more selected carrier nucleic acid strands are flowed to the surface 140 via the fluid 130. At step 622, the one or more selected carrier nucleic acid strands are recovered, retrieved or acquired from the fluid 130. In one or more embodiments, the one or more selected carrier nucleic acid strands may be recovered based on the predetermined condition for injection. For example, if the one or more selected carrier nucleic acid strands are injected into the fluid 130 based on a timed interval, the one or more selected carrier nucleic acid strands that reach the surface may be retrieved at the same timed interval, or rather, the retrieval is timed to receive the fluid 130 and replicate the one or more carrier nucleic acid strands by PCR. Very small of amounts of DNA/RNA strands are required to self-replicate. For example, only 50-250 nanograms of DNA and 1-10 nanograms for viral DNA may be required for replication. In one or more embodiments, the carrier nucleic acid strands would be retrieved from the fluid 130 received at the surface 140 prior to the fluid 130 reaching a retention pit, such as retention pit 124 of FIG. 1.

Once the fluid 130 reaches the retention pit 124, the concentration of selected carrier nucleic acid strands may drop below detectable limits. For example, the selected carrier nucleic acid strands may be diluted by other nucleic acid strands previously received at the retention pit 124. In one or more embodiments, the one or more selected carrier nucleic acid strands are injected into the fluid 130 downhole at a rate above a threshold or within a threshold range. For example, in one or more embodiments, the one or more selected carrier nucleic acid strands are injected into the fluid 130 downhole above a detectable limit threshold. In another example, in one or more embodiments, the one or more selected carrier nucleic acid strands are injected into the fluid 130 downhole above a detectable limit threshold but below a detectable background threshold (for example, detectable background due to fluid cycling of the fluid 130 in the retention pit 124). In one or more embodiments, if the one or more selected carrier nucleic acid strands do not exist in the fluid 130 received at the surface 140 above the detectable limit, the one or more selected carrier nucleic acid strands may be filtered based on one or more header data of the one or more selected carrier nucleic acid strands.

In one or more embodiments, at step 622 a nucleic acid terminator may be injected or introduced to the fluid 130 to stop the nucleic acid strands in the fluid 130 from replicating. For example, the nucleic acid terminator may be injected or introduced into the retention pit 124. In one or more embodiments, a biological chemical may be introduced into the fluid 130 of the retention pit 124 to clean the nucleic acid strands. The nucleic acid terminator may be introduced based on predetermined criteria, for example, a time interval, completion of an operation, or if the background level of nucleic acid rises to a threshold indicative of interference in decoding signals, or any other criteria.

At step 624, the recovered, retrieved or acquired carrier nucleic acid strands are decoded, read, analyzed or otherwise interpreted by a surface control system. PCR can typically be run within a predetermined interval of time, for example, ten to twenty minutes, allowing all coded information in the one or more selected carrier DNA/RNA strands that reach the surface 140 to be decoded, analyzed, or read within a short time frame. The decoded carrier nucleic acid strands with segments or sections that include a header may be reconstructed based on the header.

At step 628, one or more operations may be adjusted or altered based, at least in part, on the read, analyzed or decoded recovered, retrieved, or acquired one or more selected carrier nucleic acid strands. The one or more operations may comprise a drilling operation, a steering operation of a drill bit, an LWD operation, a MWD operation, type, concentration or mixture of fluid flowed downhole, formation evaluation including reservoir evaluation and sampling operations, any other suitable operation and any combination thereof. For example, analysis of the downhole information obtained from the recovered, retrieved, or acquired one or more selected carrier nucleic acid strands may indicate that a drilling operation should be altered or adjusted to obtain a desired or predetermined drilling direction.

The present disclosure provides one or more embodiments for the improvement of accuracy and increased efficiency in the communication of downhole information to the surface. In one or more embodiments, any one or more aspects of the present invention may be utilized in conjunction with or redundantly to any other telemetry technique including, but not limited to, mud pulsed telemetry. In one or more embodiments, parallel telemetry channels may be utilized that allow for a telemetry rate that exceeds current mud pulsed telemetry rates. For example, thousands of encoded nucleic acid strands may be injected into a fluid, for example, fluid 130 of FIG. 2, simultaneously from multiple telemetry modules, for example, telemetry system 134 of FIG. 2 or from a microfluidic chip, for example, microfluidic chip 202 of FIG. 5, where the substituted nucleic acid strands are akin to the pages of a book.

The present disclosure contemplates that any one or more steps of FIG. 6 may be performed in any suitable order or may be repeatedly performed according to a particular operation.

Figure 7:
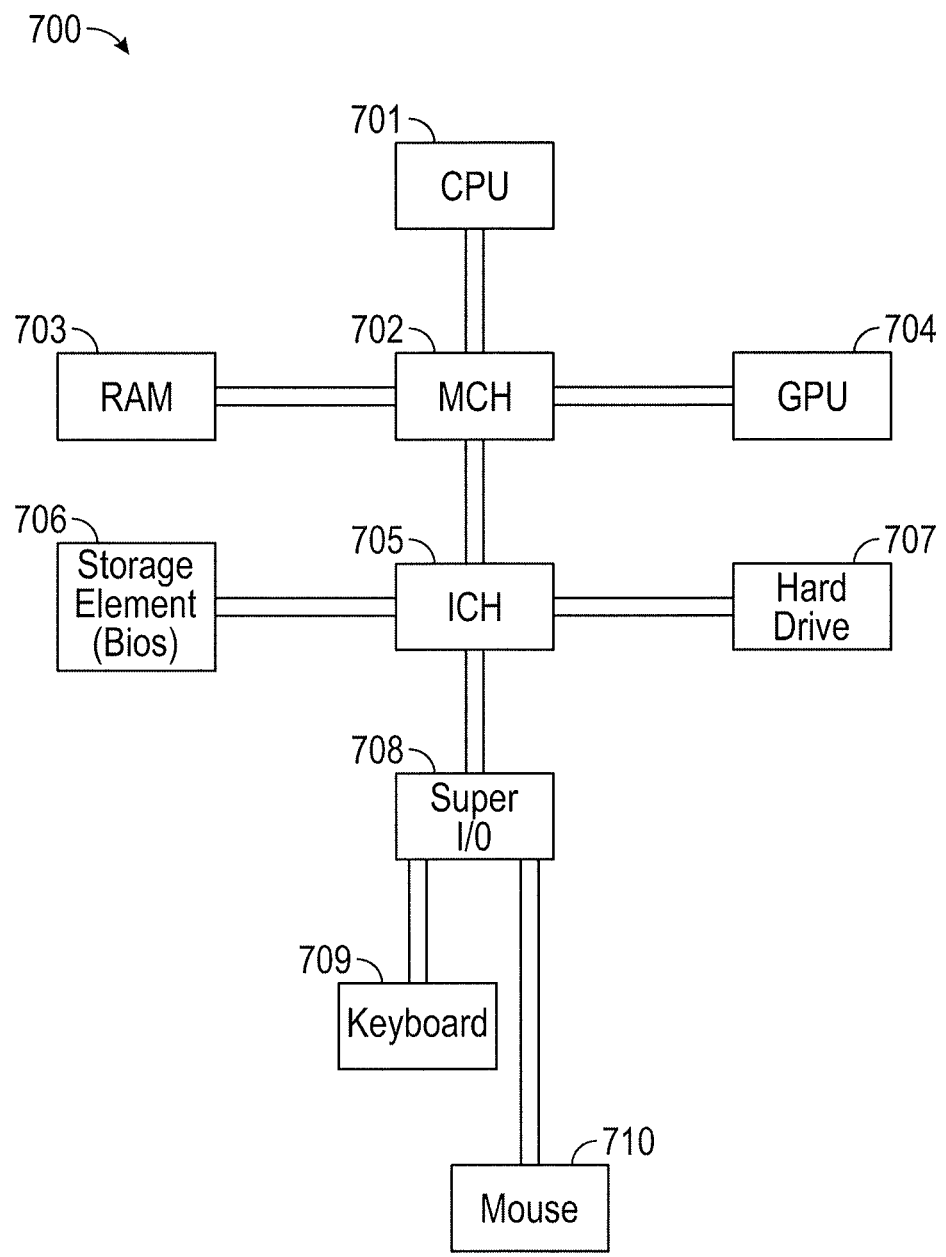
FIG. 7 depicts an example information handling system, according to one or more aspects of the present disclosure.
Figure 8:
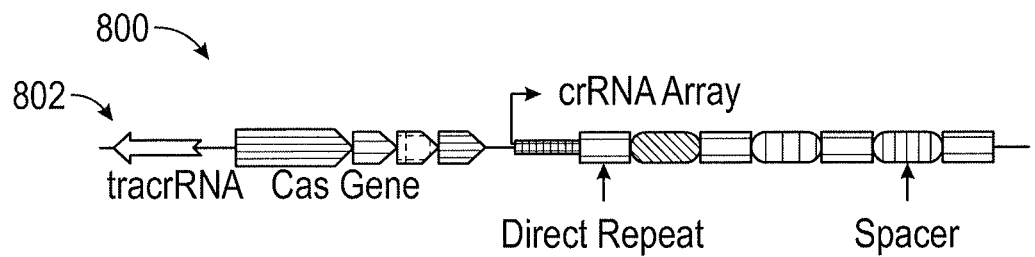
FIG. 8 depicts a nucleic acid encoding method, according to one or more aspects of the present disclosure.
Figure 8:
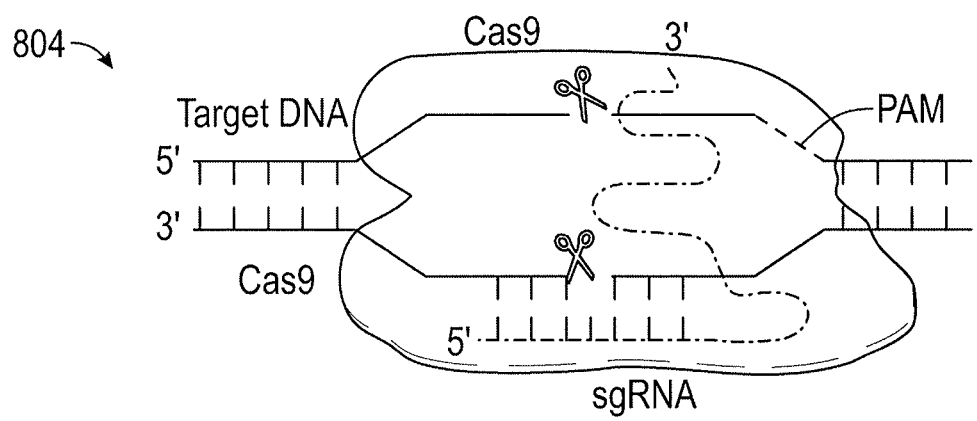
Figure 8:
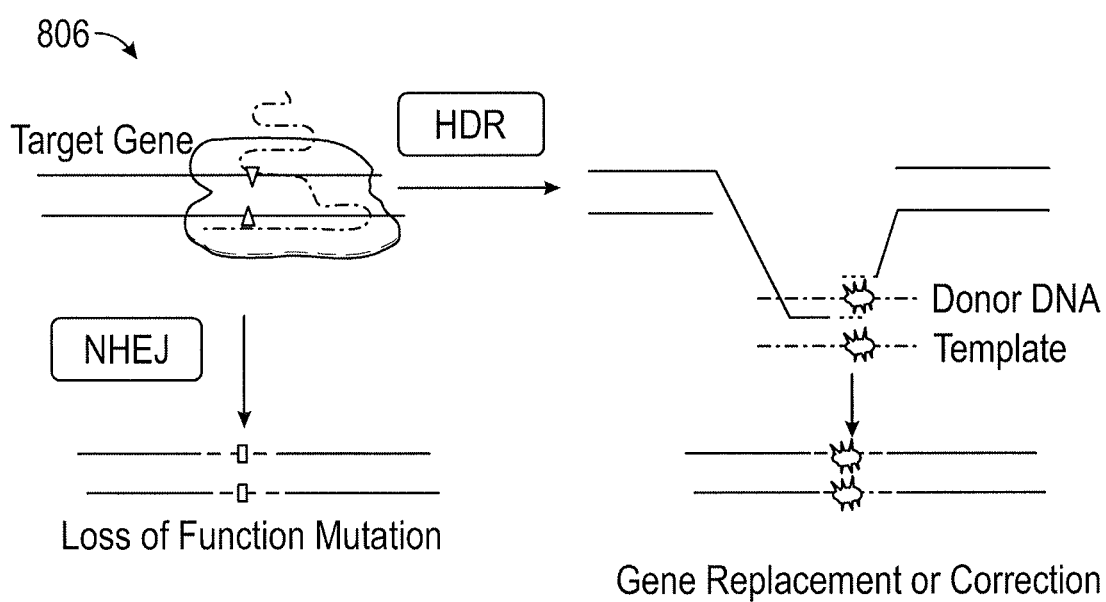

FIG. 7 is a diagram illustrating an example information handling system 700, according to one or more aspects of the present disclosure. The control system 222 may take a form similar to the information handling system 700. A processor or central processing unit (CPU) 701 of the information handling system 700 is communicatively coupled to a memory controller hub (MCH) or north bridge 702. The processor 701 may include, for example a microprocessor, microcontroller, digital signal processor (DSP), application specific integrated circuit (ASIC), or any other digital or analog circuitry configured to interpret and/or execute program instructions and/or process data. Processor 701 may be configured to interpret and/or execute program instructions or other data retrieved and stored in any memory such as memory 703 or hard drive 707. Program instructions or other data may constitute portions of a software or application for carrying out one or more methods described herein. Memory 703 may include read-only memory (ROM), random access memory (RAM), solid state memory, or disk-based memory. Each memory module may include any system, device or apparatus configured to retain program instructions and/or data for a period of time (for example, computer-readable non-transitory media). For example, instructions from a software or application may be retrieved and stored in memory 403 for execution by processor 701.

Modifications, additions, or omissions may be made to FIG. 7 without departing from the scope of the present disclosure. For example, FIG. 7 shows a particular configuration of components of information handling system 700. However, any suitable configurations of components may be used. For example, components of information handling system 700 may be implemented either as physical or logical components. Furthermore, in some embodiments, functionality associated with components of information handling system 700 may be implemented in special purpose circuits or components. In other embodiments, functionality associated with components of information handling system 700 may be implemented in configurable general-purpose circuit or components. For example, components of information handling system 700 may be implemented by configured computer program instructions.

Memory controller hub 702 may include a memory controller for directing information to or from various system memory components within the information handling system 700, such as memory 703, storage element 706, and hard drive 707. The memory controller hub 702 may be coupled to memory 703 and a graphics processing unit (GPU) 704. Memory controller hub 702 may also be coupled to an I/O controller hub (ICH) or south bridge 705. I/O controller hub 705 is coupled to storage elements of the information handling system 700, including a storage element 706, which may comprise a flash ROM that includes a basic input/output system (BIOS) of the computer system. I/O controller hub 705 is also coupled to the hard drive 707 of the information handling system 700. I/O controller hub 705 may also be coupled to a Super I/O chip 708, which is itself coupled to several of the I/O ports of the computer system, including keyboard 709 and mouse 710.

FIG. 8 depicts a nucleic acid encoding method 800, according to one or more aspects of the present disclosure. For example, FIG. 8 illustrates a CRISPR/Cas9 method for DNA/RNA segment or section substitution as discussed above with respect to step 606 of FIG. 6. At 802, a location is targeted. As illustrated, a Type II system uses a transactivating RNA (tracrRNA) to make the CRISPR RNA (crRNA) or substitute RNA segment or section. The substitute RNA segment or section at 802 has a certain sequence that aligns with a carrier DNA segment or section. At 802, Cas gene on the RNA segment is illustrated. A Cas system provides a way to locate and open up a DNA molecule for substitution and acts as an activator and also a locating method. The Cas molecule of 802 is coded specifically to substitute to a location along a DNA segment.

At 804 a section of DNA is opened at a specific or predetermined location and a segment for isolation is isolated. The CRISPR/Cas9 method, for example, requires a protospacer adjacent motif (PAM). As illustrated the PAM is not present in the single guide RNA (sgRNA) sequence. The Cas9 in 804 comprises one or more activation substances 805 as discussed above. At 806, the target DNA segment is replaced, and the DNA molecule is closed. "HDR" represents the homology directed repair pathway and "NHEJ" represents the non-homologous end joining pathway. At 806, a DNA molecule (target gene) is opened up at HDR. The "Donor DNA template" illustrated at 806 is the substitute DNA segment or section.

An embodiment of the present disclosure is a downhole telemetry system that includes a nucleic acid encoding system comprising an encoder, wherein the encoder fluidically couples a first repository comprising one or more carrier nucleic acid strands, a second repository comprising one or more nucleic acid segments and a third repository comprising one or more activation substances; and a control system coupled to the encoder, wherein the control system controls mixing the one or more carrier nucleic acid segments, the one or more nucleic acid segments and the one or more activation substances to form one or more encoded carrier nucleic acid strands. The downhole telemetry system also includes an output port coupled to the nucleic acid encoding system; and a fluid, wherein the fluid communicates the one or more encoded carrier nucleic acid strands to a surface through the output port. In one or more embodiments described above, the downhole telemetry system includes a contrast agent. In one or more embodiments described above, the encoder comprises a microfluidic chip. In one or more embodiments described above, the one or more encoded carrier nucleic acid strands is encapsulated in one or more capsules. In one or more embodiments described above, the control system forms one or more encoded carrier nucleic acid strands by implementing a clustered regularly interspaced short palindromic repeats (CRISPR)-associated protein-9 nuclease (CRISPR/Cas9) technique. In one or more embodiments described above, the control system controls mixing using a microfluidic chip. In one or more embodiments described above, at least one of the one or more activation substances promotes at least one of self-replication and editing.

Another embodiment of the present disclosure is a method of communicating downhole information to a surface that includes receiving by a nucleic acid encoding system downhole information; selecting one or more nucleic acid segments that correspond to the downhole information; selecting one or more carrier nucleic acid strands; encoding the one or more carrier nucleic acid strands with the one or more nucleic acid segments to form one or more encoded carrier nucleic acid strands; and introducing the one or more encoded carrier nucleic acid strands into a fluid to communicate the one or more encoded carrier nucleic acid strands to the surface through flow of the fluid. In one or more embodiments described above, the method includes configuring the one or more encoded carrier nucleic acid strands with a header. In one or more embodiments described above, the method includes selecting the one or more carrier nucleic acid strands based, at least in part, on a header of the one or more carrier nucleic acid strands. In one or more embodiments described above, encoding each carrier nucleic acid strand to form each encoded carrier nucleic acid strand includes at least one of inserting the one or more nucleic acid segments into the carrier nucleic acid strand and substituting one or more segments of the carrier nucleic acid strand with one or more nucleic acid segments. In one or more embodiments described above, encoding each carrier nucleic acid strand to form each encoded carrier nucleic acid strand includes a clustered regularly interspaced short palindromic repeats (CRISPR) technique. In one or more embodiments described above, the method includes injecting a contrast agent into the fluid. In one or more embodiments described above, the method includes encapsulating the one or more encoded carrier nucleic acid strands.

Another embodiment of the present disclosure is a method for analyzing downhole information that includes disposing a nucleic acid encoding tool in a wellbore; flowing a fluid in the wellbore; selecting one or more nucleic acid segments; selecting one or more carrier nucleic acid strands; encoding the one or more carrier nucleic acid strands with the one or more nucleic acid segments to form one or more encoded carrier nucleic acid strands; introducing the one or more encoded carrier nucleic acid strands into a fluid; flowing the one or more encoded carrier nucleic acid strands to the surface; retrieving the one or more encoded carrier nucleic acid strands from the fluid at the surface; and analyzing the retrieved one or more encoded carrier nucleic acid strands for downhole information. In one or more embodiments described above, the method includes encapsulating the one or more encoded carrier nucleic acid strands. In one or more embodiments described above, analyzing the retrieved one or more encoded carrier nucleic acid strands for downhole information includes decoding the encoded carrier nucleic acid strand. In one or more embodiments described above, the one or more nucleic acid segments include encoded downhole information. In one or more embodiments described above, analyzing the one or more encoded carrier nucleic acid strands is based, at least in part on a header of the one or more carrier nucleic acid strands. In one or more embodiments described above, encoding is performed using a microfluidic chip.

This discussion is directed to various embodiments of the invention. The drawing figures are not necessarily to scale. Certain features of the embodiments may be shown exaggerated in scale or in somewhat schematic form and some details of conventional elements may not be shown in the interest of clarity and conciseness. Although one or more of these embodiments may be preferred, the embodiments disclosed should not be interpreted, or otherwise used, as limiting the scope of the disclosure, including the claims. It is to be fully recognized that the different teachings of the embodiments discussed may be employed separately or in any suitable combination to produce desired results. In addition, one skilled in the art will understand that the description has broad application, and the discussion of any embodiment is meant only to be exemplary of that embodiment, and not intended to intimate that the scope of the disclosure, including the claims, is limited to that embodiment.

Certain terms are used throughout the description and claims to refer to particular features or components. As one skilled in the art will appreciate, different persons may refer to the same feature or component by different names. This document does not intend to distinguish between components or features that differ in name but not function, unless specifically stated. In the discussion and in the claims, the terms "including" and "comprising" are used in an open-ended fashion, and thus should be interpreted to mean "including, but not limited to . . . " Also, the term "couple" or "couples" is intended to mean either an indirect or direct connection. In addition, the terms "axial" and "axially" generally mean along or parallel to a central axis (e.g., central axis of a body or a port), while the terms "radial" and "radially" generally mean perpendicular to the central axis. The use of "top," "bottom," "above," "below," and variations of these terms is made for convenience but does not require any particular orientation of the components.

Reference throughout this specification to "one embodiment," "an embodiment," or similar language means that a particular feature, structure, or characteristic described in connection with the embodiment may be included in at least one embodiment of the present disclosure. Thus, appearances of the phrases "in one embodiment," "in an embodiment," and similar language throughout this specification may, but do not necessarily, all refer to the same embodiment.

Although the present invention has been described with respect to specific details, it is not intended that such details should be regarded as limitations on the scope of the invention, except to the extent that they are included in the accompanying claims.

What is claimed is:

1. A downhole telemetry system, comprising:
    a nucleic acid encoding system comprising:
        an encoder, wherein the encoder fluidically couples a first repository comprising one or more carrier nucleic acid strands, a second repository comprising one or more nucleic acid segments and a third repository comprising one or more activation substances; and
        a control system coupled to the encoder, wherein the control system controls mixing the one or more carrier nucleic acid strands, the one or more nucleic acid segments and the one or more activation substances to form one or more encoded carrier nucleic acid strands;
    an output port coupled to the nucleic acid encoding system; and
    a fluid, wherein the fluid communicates the one or more encoded carrier nucleic acid strands to a surface through the output port.

2. The system of claim 1, further comprising a contrast agent.

3. The system of claim 1, wherein the encoder comprises a microfluidic chip.

4. The system of claim 1, wherein the one or more encoded carrier nucleic acid strands is encapsulated.

5. The system of claim 1, wherein the control system forms one or more encoded carrier nucleic acid strands by implementing a clustered regularly interspaced short palindromic repeats (CRISPR)-associated protein-9 nuclease (CRISPR/Cas9) technique.

6. The system of claim 1, wherein the control system controls mixing using a microfluidic chip.

7. The system of claim 1, wherein at least one of the one or more activation substances promotes at least one of self-replication and editing.

8. A method of communicating downhole information to a surface, comprising:
    receiving by a nucleic acid encoding system downhole information;
    selecting one or more nucleic acid segments that correspond to the downhole information;
    selecting one or more carrier nucleic acid strands; and
    encoding the one or more carrier nucleic acid strands with the one or more nucleic acid segments to form one or more encoded carrier nucleic acid strands; and
    introducing the one or more encoded carrier nucleic acid strands into a fluid to communicate the one or more encoded carrier nucleic acid strands to the surface through flow of the fluid.

9. The method of claim 8, further comprising configuring at least one carrier nucleic acid strand, nucleic acid segment, or a combination thereof with a header.

10. The method of claim 8, further comprising selecting the one or more carrier nucleic acid strands based, at least in part, on a header of the one or more carrier nucleic acid strands.

11. The method of claim 8, wherein encoding each carrier nucleic acid strand to form each encoded carrier nucleic acid strand comprises at least one of inserting the one or more nucleic acid segments into the carrier nucleic acid strand and substituting one or more segments of the carrier nucleic acid strand with one or more nucleic acid segments.

12. The method of claim 8, wherein encoding each carrier nucleic acid strand to form each encoded carrier nucleic acid strand involves a clustered regularly interspaced short palindromic repeats (CRISPR) technique.

13. The method of claim 8, further comprising injecting a contrast agent into the fluid.

14. The method of claim 8, further comprising encapsulating the one or more encoded carrier nucleic acid strands.

15. A method for analyzing downhole information, comprising:
    disposing a nucleic acid encoding tool in a wellbore;
    flowing a fluid in the wellbore;
    selecting one or more nucleic acid segments;
    selecting one or more carrier nucleic acid strands; and
    encoding the one or more carrier nucleic acid strands with the one or more nucleic acid segments to form one or more encoded carrier nucleic acid strands;
    introducing the one or more encoded carrier nucleic acid strands into a fluid;
    flowing the one or more encoded carrier nucleic acid strands to the surface;
    retrieving the one or more encoded carrier nucleic acid strands from the fluid at the surface; and
    analyzing the retrieved one or more encoded carrier nucleic acid strands for downhole information.

16. The method for analyzing downhole information of claim 15, further comprising encapsulating the one or more encoded carrier nucleic acid strands.

17. The method for analyzing downhole information of claim 15, wherein analyzing the retrieved one or more encoded carrier nucleic acid strands for downhole information comprises decoding the encoded carrier nucleic acid strand.

18. The method for analyzing downhole information of claim 15, wherein the one or more nucleic acid segments comprise encoded downhole information.

19. The method for analyzing downhole information of claim 15, wherein analyzing the one or more encoded carrier nucleic acid strands is based, at least in part on a header of the one or more encoded carrier nucleic acid strands.

20. The method of claim 15, wherein the encoding is performed using a microfluidic chip.

* * * * *